US011925703B1

(12) United States Patent
Fumic et al.

(10) Patent No.: US 11,925,703 B1
(45) Date of Patent: Mar. 12, 2024

(54) LIQUID COMPOSITION COMPRISING GLUCOSE

(71) Applicant: Xellia Pharmaceuticals APS, Copenhagen (DK)

(72) Inventors: Barbara Fumic, Zagreb (HR); Stipica Tomic, Zagreb (HR)

(73) Assignee: Xellia Pharmaceuticals APS, Copenhagen (DK)

( * ) Notice: Subject to any disclaimer, the term of this patent is extended or adjusted under 35 U.S.C. 154(b) by 0 days.

(21) Appl. No.: 18/360,149

(22) Filed: Jul. 27, 2023

Related U.S. Application Data

(60) Provisional application No. 63/393,337, filed on Jul. 29, 2022.

(51) Int. Cl.
| *A61K 9/00* | (2006.01) |
| *A61K 9/08* | (2006.01) |
| *A61K 31/7004* | (2006.01) |
| *A61K 47/02* | (2006.01) |

(52) U.S. Cl.
CPC .............. *A61K 9/0029* (2013.01); *A61K 9/08* (2013.01); *A61K 31/7004* (2013.01); *A61K 47/02* (2013.01)

(58) Field of Classification Search
None
See application file for complete search history.

(56) References Cited

U.S. PATENT DOCUMENTS

| 4,548,817 | A | 10/1985 | Filley et al. | |
|---|---|---|---|---|
| 4,584,176 | A | 4/1986 | Oliver et al. | |
| 5,092,838 | A | 3/1992 | Faict et al. | |
| 5,211,643 | A | 5/1993 | Reinhardt et al. | |
| 5,296,242 | A | 3/1994 | Zander | |
| 5,827,820 | A | 10/1998 | Dumoulin et al. | |
| 6,277,815 | B1 | 8/2001 | Knerr | |
| 6,309,673 | B1 | 10/2001 | Duponchelle et al. | |
| 6,399,110 | B1 * | 6/2002 | Kikuchi | A61K 45/06 604/416 |
| 7,122,210 | B2 | 10/2006 | Elisabettini et al. | |
| 7,445,801 | B2 | 11/2008 | Faict et al. | |
| 9,161,980 | B2 | 10/2015 | Ernebrant et al. | |
| 2009/0170882 | A1 * | 7/2009 | Dhanak | A61P 37/00 548/440 |
| 2022/0151870 | A1 | 5/2022 | Adamo et al. | |

FOREIGN PATENT DOCUMENTS

| CN | 201082253 Y | 7/2008 |
|---|---|---|
| CN | 201116193 Y | 9/2008 |
| CN | 101317808 A | 12/2008 |
| CN | 101401769 A | 4/2009 |
| CN | 101618770 A | 1/2010 |
| CN | 201880025 U | 6/2011 |
| CN | 102488617 A | 6/2012 |
| CN | 102614081 A | 8/2012 |
| CN | 202366163 U | 8/2012 |
| CN | 102716147 A | 10/2012 |
| CN | 203107695 U | 8/2013 |
| CN | 203107699 U | 8/2013 |
| CN | 103754403 A | 4/2014 |
| CN | 103768091 A | 5/2014 |
| CN | 103800285 A | 5/2014 |
| CN | 104107140 A | 10/2014 |
| CN | 105030534 A | 11/2015 |
| CN | 107812012 A | 3/2018 |
| CN | 109806223 A | 5/2019 |
| CN | 110638831 A | 1/2020 |
| WO | 8103180 A1 | 11/1981 |
| WO | 9425084 A1 | 11/1994 |
| WO | 9629103 A1 | 9/1996 |
| WO | 9841218 A1 | 9/1998 |
| WO | 03059417 A1 | 7/2003 |
| WO | 2019113543 A1 | 6/2019 |
| WO | 2022183055 A1 | 9/2022 |

OTHER PUBLICATIONS

Hill, A. et al.; "Sodium Carbonate, Sodium Bicarbonate and Water"; Ternary Systems, VI, vol. 49; 1927; pp. 2487-2495.
Sayre, B. et al.; "Extended Stability of Sodium Bicarbonate Infusions Prepared in Polyolefin Bags"; Hospital Pharmacy, vol. 47, Issue No. 7; 2012; pp. 538-543; DOI:10.1310/hpj4707-538.
Wear, J. et al.; "Stability of sodium bicarbonate solutions in polyolefin bags"; American Journal of Health-System Pharmacy, vol. 67; 2010; pp. 1026-1029; DOI:10.2146/ajhp090301.

* cited by examiner

*Primary Examiner* — Dale R Miller
(74) *Attorney, Agent, or Firm* — Karen A. LeCuyer; DeWitt LLP

(57) ABSTRACT

The present disclosure relates to an aqueous composition stored in a single unit dosage container, where the aqueous composition consists of glucose, sodium bicarbonate, water, and a pH adjusting agent if needed to adjust the pH, wherein the pH of the composition is from 6.7 to 8.1. Such composition is stable for at least 3 months at room temperature conditions.

15 Claims, No Drawings

LIQUID COMPOSITION COMPRISING GLUCOSE

CROSS-REFERENCE TO RELATED APPLICATIONS

This application claims priority to U.S. Provisional Application 63/393,337 filed on Jul. 29, 2022, which is incorporated herein by reference in its entirety.

FIELD OF THE INVENTION

The present disclosure relates to liquid compositions comprising glucose.

BACKGROUND

Glucose (dextrose) is one of the pharmaceutical ingredients used in parenteral drugs as a tonicity or osmolality agent. Although glucose is used parenterally, its use in parenteral liquid compositions has its drawbacks. For instance, some of the isomerization/degradation products could be a potential risk to certain populations of patients. Isomerization/degradation products of glucose include fructose, 5-hydroxymethylfurfural (5-HMF), mannose, and the like.

Isomerization/degradation of glucose in liquid, aqueous compositions may be dependent on several factors, including the temperature, the pH of the liquid, the concentration of glucose, and others. One of the factors with a major influence on the isomerization/degradation of glucose is the pH of the composition. It is known that a high pH of the liquid has a negative effect on glucose stability. This is especially a problem when glucose is added to a solution in which the pH needs to be high, for example where the pH must be higher than 6.5.

This problem has been addressed in the prior art by providing two separate containers for storage, where in the first container glucose is in a liquid having a low pH, and in the second container the other components are in a liquid having a high pH. Such separate containers are to be mixed just before administration.

Thus, one of the drawbacks of the existing liquid formulations having a high pH and comprising glucose is that they require mixing of at least two separate containers prior to being administered to a patient, thus increasing the risk of medication errors, needlestick injuries, and possible infections.

Thus, there is a need for a ready-to-administer liquid glucose composition having a high pH which would be free or substantially free of glucose degradation/isomerization products. Also, there is a need for a ready-to-administer liquid composition comprising glucose and having a high pH which could be delivered to patient population groups in which degradation/isomerization product of glucose may be a potential risk.

SUMMARY

The present disclosure relates to a liquid composition, e.g., an aqueous composition, comprising glucose. Specifically, the present disclosure relates to a ready-to-administer composition comprising glucose.

According to the present disclosure, isomerization/degradation of glucose is retarded, and the shelf life of such product is prolonged.

The liquid composition according to the present disclosure may further comprise at least one pharmaceutical ingredient.

In one aspect, the pH of the liquid composition is from 6.7 to 8.5.

In one aspect, the composition is in a single unit dosage form.

The disclosed formulations may have enhanced activity and/or efficacy.

The present disclosure is also related to a method of producing a liquid composition comprising glucose as well as to a method of treatment of patients in need thereof with compositions comprising glucose.

DETAILED DESCRIPTION

By the terms "pharmaceutical composition" or "pharmaceutically acceptable composition" as used herein, is meant any composition suitable and intended for in vivo use, for example administration to a patient or a subject. As used herein, the terms "patient" and "subject" are interchangeable and refer to any human or animal individual who is receiving a composition as described herein.

As used herein, the terms "pharmaceutical composition", "pharmaceutically acceptable composition", "pharmaceutical formulation", "composition" and "formulation" are used interchangeably.

A "ready-to-administer" composition is synonymous with "ready-to-infuse" or "ready-to-inject" and is not to be read as the term "ready-to-use" composition. A "ready-to-administer" composition is suitable for administration directly to the patient and does not require any mixing or dilution steps.

The term "ready-to-administer" is also distinguished from lyophilized products that typically require two steps, a first step of reconstitution to form a preconcentrate and then a second step where the preconcentrate is subjected to dilution with a liquid infusion fluid.

The present disclosure relates to liquid composition comprising glucose.

According to the present invention, degradation/isomerization of glucose is retarded, and the shelf life of such composition is prolonged.

The liquid composition described herein may be administered to a patient, such as a human patient, preferably directly without any mixing or dilution steps. The liquid composition according to the present disclosure may further comprise at least one pharmaceutical ingredient.

In an aspect, the pH of the liquid composition is from 6.7 to 8.5.

In an aspect, the pH of the liquid composition is from 6.7 to 8.1. In an aspect, the pH of the liquid composition is from 6.7 to 7.7. In an aspect, pH of the composition is 6.7, 6.8, 6.9, 7.0. 7.1, 7.2, 7.3, 7.4, 7.5, 7.6, 7.7, 7.8, 7.9, 8.0, 8.1, 8.2, 8.3, 8.4 or 8.5.

In an aspect, the inventors found that in compositions where the pH does not shift or does not shift significantly over time, the glucose will be stable or will be less degraded and the product will be more stable over time compared to products which experience a significant pH shift. In one aspect, in a range of pH 6.7 to 8.1 and where pH does not change by more than 0.3 units pH over time, isomerization/degradation of glucose is low. In another aspect, in a range of pH 6.7 to 7.7 and where the pH does not change by more than 0.3 units pH over time, isomerization/degradation of glucose is low. In an aspect, the pH remains within the target pH range, e.g., pH 6.7 to 8.1, even when there is a pH shift over time.

In one aspect, the pH does not change by more than 1 unit while remaining within the target pH range of the composition when stored for at least 3 months at room temperature.

By the term "room temperature" is meant a temperature from 20° C. to 25° C.

In one aspect, the pH does not change by more than 0.3 units in at least 3 months at room temperature while remaining within the target pH range of the composition.

In one aspect, the pH does not change by more than 1 unit while remaining within the target pH range of the composition when stored for at least 6 months at room temperature.

In one aspect, the pH does not change by more than 0.2 units while remaining within the target pH range of the composition when stored for at least 3 months at room temperature.

In an aspect, when a pH is recited, for example, a pH of 6.7 to 8.5, the pH remains between a pH of 6.7 to 8.5 when stored for at least 3 months at room temperature, or at least 6 months at room temperature.

In an aspect, when a pH is recited, for example, a pH of 6.7 to 8.1, the pH remains between a pH of 6.7 to 8.1 when stored for at least 3 months at room temperature, or at least 6 months at room temperature.

In an aspect, when a pH is recited, for example, a pH of 6.7 to 7.7, the pH remains between a pH of 6.7 to 7.7 when stored for at least 3 months at room temperature, or at least 6 months at room temperature.

"pH" is the conventional measurement unit of hydrogen ion activity in a solution at room temperature, unless another temperature is specified.

As used herein, the term "pH" of a composition is defined as ±0.1 of the numerical value or range in question.

In one aspect, the composition is in unit dosage form.

In one aspect, glucose may be glucose, glucose monohydrate or anhydrous glucose. If not otherwise stated, calculations of molar ratio or concentrations of glucose in the present disclosure are done based on glucose anhydrous.

In one aspect, glucose is glucose monohydrate.

In one aspect, glucose is anhydrous glucose.

It was found that, when glucose is formulated in formulations according to the present disclosure, isomerization/degradation product formation is retarded, and accordingly, such formulations exhibit prolonged chemical and physical stability and provide more flexible storage conditions and handling when stored under room temperature conditions. In one aspect, the pharmaceutical formulation in accordance with the present disclosure has improved stability at a temperature of 30° C.

Further, the pharmaceutical formulation in accordance with the present disclosure has improved stability at a temperature of 40° C.

The term "stable" means that the pharmaceutical compositions meet one or more of the following criteria:
  (i) The pharmaceutical composition exhibits an acceptable amount of glucose degradation after a certain period of time compared to the amount of glucose present at the beginning of the period of time; and/or
  (ii) the pharmaceutical composition exhibits an acceptable amount of impurities being formed after a certain period of time compared to the amount of impurities present at the beginning of the period of time.

In one aspect, a liquid formulation according to the present disclosure is stable under room temperature conditions for a certain period of time.

In one aspect, the compositions are stable for at least at least 1 month, at least 2 months, at least 3 months, at least 6 months, at least 9 months, or at least 12 months, or longer, when stored at room temperature conditions.

In one aspect, the compositions are stable for at least 3 months when stored at room temperature conditions.

Formulations according to the present disclosure showed surprising stability for a defined period of time, when stored at a temperature of 30° C.

In one aspect, the compositions are stable for at least 1 month, at least 2 months, at least 3 months, or at least 6 months, when stored at temperature of 30° C.

In one aspect, the compositions are stable for at least 1 month when stored at a temperature of 30° C.

Formulations according to the present disclosure showed surprising stability for a reasonable period of time, when stored at a temperature of 40° C.

In one aspect, the compositions are stable for at least 1 month, at least 2 months, at least 3 months or more when stored at a temperature of 40° C.

In one aspect, the compositions are stable for at least 1 month when stored at a temperature of 40° C.

In one aspect, pharmaceutical compositions described herein are stable for at least 24 hours at temperature of 60° C.

In one aspect, "stability" may be defined by the amount of total or individual impurities in the formulation after a certain period of time. Stability may also be defined by increase of total or individual impurities generated after a defined period of time.

The stability may be determined by measuring the amount of an individual impurity in the formulation according to the present disclosure after a predetermined time period, preferably expressed as a percentage, for example as a peak-area percentage of a chromatogram.

By the term "impurity" as used herein is meant an isomerization/degradation impurity of glucose in the formulation.

The impurities present in the formulation may be expressed as a percentage, for example as a peak-area percentage of a HPLC chromatogram. The term HPLC also include ultra-high performance liquid chromatography (UHPLC).

The disclosed formulations minimize degradation/isomerization of glucose to impurities.

As used herein, "stable" may be defined as less than or equal to a 10% of chromatographic purity decrease/drop of glucose in the pharmaceutical formulation, determined by HPLC analysis.

For example, a stable composition can be one which has less than or equal to a 1%, 2%, 3%, 4%, 5%, 6%, 7%, 8%, 9%, or 10% purity decrease/drop of glucose, determined by HPLC analysis after a predetermined time period.

In an aspect, a stable composition can be one which has less than or equal to an 8% purity decrease/drop of glucose ingredient, determined by HPLC analysis after a predetermined time period.

In an aspect, a stable composition can be one which has less than or equal to a 5% purity decrease/drop of glucose, determined by HPLC analysis after a predetermined time period.

In another aspect, "stable" may be defined as less than or equal to a 5% increase (expressed as peak-area percentage) of individual impurity formation, determined by HPLC analysis after a predetermined time period.

In another aspect, "stable" may be defined as less than or equal to a 2% increase (expressed as peak-area percentage) of individual impurity formation, determined by HPLC analysis after a predetermined time period.

In one aspect, a stable composition can be one that has less than or equal to a 0.2%, 0.3%, 0.4%, 0.5%, 0.7%, 1%, 2%, 3%, 4%, 5%, increase (expressed as peak-area percentage) of individual impurity formation, determined by HPLC analysis after a predetermined time period.

One of the glucose impurities is fructose. Fructose is a main isomerization product of glucose, which might impact both the safety and the efficacy of the pharmaceutical composition.

In one aspect, a stable composition can be one that has less than or equal to a 0.2%, 0.3%, 0.4%, 0.5%, 0.7%, 1%, 2%, 3%, 4%, or 5%, increase (expressed as peak-area percentage) of fructose, determined by HPLC analysis after a predetermined time period.

In one aspect, a stable or stabilized composition comprising glucose may be one that has less than or equal to a 2% increase of fructose, determined by HPLC analysis after storage for 3 months and longer at room temperature.

In one aspect, a stable or stabilized composition comprising glucose may be one that has less than or equal to a 1% increase of fructose, determined by HPLC analysis after storage for 3 months and longer at room temperature.

In one aspect, a stable or stabilized composition comprising glucose may be one that has less than or equal to a 0.5% increase of fructose, determined by HPLC analysis after storage for 3 months and longer at room temperature.

In one aspect, a stable or stabilized composition comprising glucose may be one that has less than or equal to a 2% increase of fructose, determined by HPLC analysis after storage for 6 months and longer at room temperature.

In one aspect, a stable or stabilized composition comprising glucose may be one that has less than or equal to a 1% increase of fructose, determined by HPLC after storage for 6 months and longer at room temperature.

In one aspect, a stable or stabilized composition comprising glucose may be one that has less than or equal to a 0.5% increase of fructose, determined by HPLC after storage for 6 months and longer at room temperature.

In one aspect, a stable or stabilized composition comprising glucose may be one that has less than or equal to a 2% increase of fructose, determined by HPLC analysis after storage for 3 months and longer at 30° C.

In one aspect, a stable or stabilized composition comprising glucose may be one in which a sample solution has an absorbance of less than or equal to 0.25 at 284 nm of 5-HMF after storage for 3 months and longer at room temperature when tested in accordance with the USP monograph for dextrose injection as official from Jan. 1, 2022.

In one aspect, a stable or stabilized composition comprising glucose may be one in which a sample solution has an absorbance of less than or equal to 0.25 at 284 nm of 5-HMF after storage for 3 months and longer at 30° C., when tested in accordance with the USP monograph for dextrose injection as official from Jan. 1, 2022.

In an aspect, a stable or stabilized composition may be one wherein the purity of glucose after a certain period of time is at least 90%, determined by HPLC analysis.

In an aspect, a stable or stabilized composition can be one wherein the purity of glucose after storage for 2 months at room temperature is at least 95%, determined by HPLC analysis.

In an aspect, a stable or stabilized composition can be one wherein the purity of glucose present after storage for 3 months at room temperature is at least 95%, determined by HPLC analysis.

In an aspect, a stable or stabilized composition can be one wherein the purity of glucose present after storage for 3 months at 40° C. is at least 95%, determined by HPLC analysis.

In an aspect, a stable or stabilized composition can be one wherein the purity of glucose present after storage for 12 months at room temperature is least 97%, determined by HPLC analysis.

In one aspect, the pharmaceutical composition according to this disclosure is stable after storage for at least 3 months at room temperature.

In one aspect, the pharmaceutical composition according to this disclosure is stable after storage for at least 6 months at room temperature.

In one aspect, the pharmaceutical composition comprising glucose is stable after storage for at least 3 months at room temperature, as demonstrated by determining the amount of fructose and 5-HMF present in the pharmaceutical composition at 3 months, and wherein the amount of the fructose present after 3 months is less than or equal to 3% and where a sample solution of the formulation has an absorbance of less than or equal to 0.25 at 284 nm of 5-HMF after 3 months when tested in accordance with the USP monograph for dextrose injection as official from Jan. 1, 2022.

In one aspect, the pharmaceutical composition comprising glucose and having a pH from 6.7 to 8.5 is stable after storage for at least 3 months at room temperature, as demonstrated by determining the amount of fructose and 5-HMF present in the pharmaceutical composition at 3 months, and wherein the amount of the fructose present after 3 months is less than or equal to 3% and where a sample solution of the formulation has an absorbance of less than or equal to 0.25 at 284 nm of 5-HMF after 3 months when tested in accordance with the USP monograph for dextrose injection as official from Jan. 1, 2022.

In one aspect, the pharmaceutical composition comprising glucose is stable after storage for at least 3 months at room temperature, as demonstrated by determining the amount of fructose present in the pharmaceutical composition at 3 months, and wherein the amount of the fructose present after 3 months is less than or equal to 1%, determined by HPLC analysis.

Analysis of the formulations described herein can be performed using techniques known in the art, including HPLC and potentiometric titration.

In one aspect, the concentration of glucose in the liquid formulation may be from 1 to 50 mg/ml.

In one aspect, the concentration of glucose in the liquid formulation may be from 5 to 50 mg/ml.

In one aspect, the concentration of glucose in the liquid formulation may be from 15 to 40 mg/ml.

In one aspect, the concentration of glucose in the composition may be 15 mg/ml, 15.5 mg/ml, 16 mg/ml, 17 mg/ml, 18 mg/ml, 19 mg/ml, 20 mg/ml, 22 mg/ml, 24 mg/ml, 26 mg/ml, 28 mg/ml, 30 mg/ml, 32 mg/ml, 34 mg/ml, 35 mg/ml, 36.6 mg/ml, 38 mg/ml, or 40 mg/ml.

The compositions may be in the form of a ready-to-administer composition.

In an aspect, the pharmaceutical formulation is aqueous.

By the term "aqueous composition", "aqueous solution" or "aqueous" is understood any composition in which water is present in or above 50% v/v, such as, e.g., a composition comprising from 50% v/v to 99.5% v/v water, from 50% v/v to 90% v/v, from 60% v/v to 85% v/v, from 70% v/v to 80% v/v water. Accordingly, aqueous compositions include compositions comprising 50% v/v or more, 60% v/v or more, 70% v/v or more, 75% v/v or more, 80% v/v or more, 85% v/v or more, 90% v/v or more, 95% v/v or more, or 99% v/v water or more.

In one aspect, an aqueous composition comprises 90% or more water.

In an aspect, a liquid composition may comprise a pH adjusting agent such as a buffer if needed to adjust the pH. In one aspect, pH adjusting agents or buffers having a buffering capacity at a pH of approximately in range from 6.7 to 8.5 may be used.

In one aspect, the liquid formulation may comprise chloride salts, phosphate or bicarbonate salts.

In one aspect, the salts may be sodium salts.

In one aspect, the liquid formulation comprises bicarbonate salts.

In one aspect, the liquid formulation comprises sodium bicarbonate.

In one aspect, the liquid formulation comprises chloride salts such as sodium chloride.

In one aspect, the formulation consists of glucose, sodium bicarbonate, water, and a pH control agent if needed to adjust the pH, that is, only glucose, sodium bicarbonate, water, and a pH control agent if needed, are admixed to provide the formulation.

In one aspect, glucose and a bicarbonate salt are in a molar ratio of 1:0.1 to 1:5.

In other aspect, glucose and a bicarbonate salt are in a molar ratio of 1:0.1 to 1:1. In other aspect, glucose and sodium bicarbonate are in a molar ratio of 1:0.2 to 1:0.8.

In one aspect glucose and sodium bicarbonate salt are in a molar ratio of 1:01, 1:02, 1:0.5, 1:0.8, 1:1, 1:2, 1:3, 1:4 or 1:5.

In one aspect, the concentration of bicarbonate ions in the liquid formulation is from 2 mg/ml to 100 mg/ml.

In one aspect, the concentration of sodium bicarbonate in the liquid formulation is from 2 mg/ml to 100 mg/ml.

In one aspect, the concentration of sodium bicarbonate in the liquid formulation is from 2 mg/ml to 15 mg/ml.

In one aspect, the concentration of sodium bicarbonate in the liquid formulation is from 4 mg/ml to 15 mg/ml.

In one aspect, the concentration of sodium bicarbonate in the liquid formulation is from 4.2 mg/ml to 12.6 mg/ml.

In one aspect, the concentration of sodium bicarbonate in the liquid formulation is from 4 mg/ml to 10 mg/ml.

In one aspect, the concentration of sodium bicarbonate in the liquid formulation is 2 mg/ml, 3 mg/ml, 4 mg/ml, 5 mg/ml, 6 mg/ml, 7 mg/ml, 8 mg/ml, 9 mg/ml, 10 mg/ml, 11 mg/ml, or 12.6 mg/ml.

In one aspect, the concentration of sodium bicarbonate in the liquid formulation is selected from 12. 6, 8.4 mg/ml and 4.2 mg/ml.

In one aspect, the composition comprises glucose and sodium bicarbonate and has less than or equal to a 0.5%, 1%, 2%, 3%, 4%, 5%, 6%, 7%, 8%, 9%, 10% purity decrease/drop of glucose after a predetermined time period.

In one aspect, the composition comprises glucose and sodium bicarbonate, wherein a % targeted concentration of sodium bicarbonate is at least 95% after a predetermined time period.

In another aspect, glucose and at least one chloride salt are in molar ratio of 1:0.5 to 1:10.

In other aspects, glucose and at least one chloride salt are in a molar ratio of 1:0.5 to 1:5. In one aspect glucose and at least one chloride salt are in a molar ratio of 1:0.5, 1:1, 1:2, 1:3, 1:4, 1:5, 1:6, 1:7, 1:8, 1:9, 1:10.

In one aspect, the pharmaceutical composition comprising glucose and sodium bicarbonate is stable after storage for at least 3 months at room temperature, as demonstrated by determining the amount of fructose present in the pharmaceutical composition at 3 months, and wherein the amount of the fructose present after 3 months is less than or equal to 1%.

In one aspect, the pharmaceutical composition comprises glucose and sodium bicarbonate and where the composition has a pH from 6.7 to 8.5, and the composition is stable after storage for at least 3 months at room temperature, as demonstrated by determining the amount of fructose present in the pharmaceutical composition at 3 months, and wherein the amount of the fructose present after 3 months is less than or equal to 1%.

In one aspect, the pharmaceutical composition comprises glucose and sodium bicarbonate and where the composition has a pH from 6.7 to 8.5, and the pH does not change by more than 0.3 pH units after storage for at least 3 months at room temperature, is stable after storage for at least 3 months at room temperature, as demonstrated by determining the amount of fructose present in the pharmaceutical composition at 3 months, and wherein the amount of the fructose present after 3 months is less than or equal to 1%.

In one aspect, the pharmaceutical composition comprising glucose and sodium bicarbonate is stable after storage for at least 3 months at room temperature, as demonstrated by determining the amount of fructose and 5-HMF present in the pharmaceutical composition at 3 months, and wherein the amount of the fructose present after 3 months is less than or equal to 3% and where a sample solution of the formulation has an absorbance of less than or equal to 0.25 at 284 nm of 5-HMF after 3 months when tested in accordance with the USP monograph for dextrose injection as official from Jan. 1, 2022.

In one aspect, the pharmaceutical composition comprises glucose and sodium bicarbonate, and where the composition having a pH from 6.7 to 8.5 is stable after storage for at least 3 months at room temperature, as demonstrated by determining the amount of fructose and 5-HMF present in the pharmaceutical composition at 3 months, and wherein the amount of the fructose present after 3 months is less than or equal to 3% and where a sample solution of formulation has an absorbance of less than or equal to 0.25 at 284 nm of 5-HMF after 3 months when tested in accordance with the USP monograph for dextrose injection as official from Jan. 1, 2022.

In one aspect, the pharmaceutical composition comprises glucose and sodium bicarbonate, and where the composition has a pH from 6.7 to 8.5 and where pH does not change by more than 0.3 pH units after storage for at least 3 months at room temperature, and the composition is stable for at least 3 months at room temperature as demonstrated by determining the amount of fructose and 5-HMF present in the pharmaceutical composition at 3 months, and wherein the amount of the fructose present after 3 months is less than or equal to 3% and where a sample solution of formulation has an absorbance of less than or equal to 0.25 at 284 nm of 5-HMF after 3 months when tested in accordance with the USP monograph for dextrose injection as official from Jan. 1, 2022.

The pH of the solutions can be adjusted in any suitable manner. Depending on the acidity or alkalinity of the composition ingredients, the predetermined pH of the composition may be adjusted with one or more pH adjusting agents, which may be selected from mineral acids, organic acids, weak and strong bases, and salts thereof. Examples of pH adjusting agents include carbon dioxide, hydrochloric acid, phosphoric acid, sulfuric acid, nitric acid, hydrogen bromide, hydrogen iodide, acetic acid, succinic acid, lactic acid, citric acid, phenolic acids, sodium hydroxide, ammonium hydroxide, and the like.

In one aspect, pH is adjusted with sodium hydroxide and hydrochloric acid.

In one aspect, pH is adjusted with carbon dioxide.

In one aspect, the pharmaceutical composition comprises glucose and sodium bicarbonate, where the pH is from 6.7 to 8.5, and where pH is optionally adjusted with carbon dioxide, wherein the composition is stable after storage for at least 3 months at room temperature, as demonstrated by determining the amount of fructose present in the pharmaceutical composition at 3 months, and wherein the amount of the fructose present after 3 months is less than or equal to 1%.

In one aspect, the pharmaceutical composition consists of glucose, sodium bicarbonate, water, and the pH is adjusted with carbon dioxide to pH 6.7 to 7.7.

In one aspect, the pharmaceutical composition consists of water, glucose and sodium bicarbonate, where pH is from 6.7 to 8.5, and where pH is optionally adjusted with a pH adjusting agent such as carbon dioxide, where the composition is stable after storage for at least 3 months at room temperature, as demonstrated by determining by HPLC analysis the amount of fructose present in the pharmaceutical composition at 3 months, and wherein the amount of the fructose present after 3 months is less than or equal to 1%.

In one aspect, the pharmaceutical composition consists of glucose, sodium bicarbonate, and water, where pH is from 6.7 to 8.1, and where pH is adjusted with a pH adjusting agent such as carbon dioxide, where the composition is stable after storage for at least 3 months at room temperature, as demonstrated by determining by HPLC analysis the amount of fructose present in the pharmaceutical composition at 3 months, and wherein the amount of the fructose present after 3 months is less than or equal to 1%.

In one aspect, the pharmaceutical composition consists of glucose, sodium bicarbonate, and water, where pH is from 6.7 to 8.1 and where pH is adjusted with a pH adjusting agent such as carbon dioxide, where the composition is stable after storage for at least 3 months at room temperature, as demonstrated by determining by HPLC analysis the amount of fructose present in the pharmaceutical composition at 3 months, and wherein the amount of the fructose present after 3 months is less than or equal to 3%.

In one aspect, the pharmaceutical composition consists of glucose, sodium bicarbonate, and water, where pH is from 6.7 to 7.7 and where pH is adjusted with a pH adjusting agent such as carbon dioxide, where the composition is stable after storage for at least 3 months at room temperature, as demonstrated by determining by HPLC analysis the amount of fructose present in the pharmaceutical composition at 3 months, and wherein the amount of the fructose present after 3 months is less than or equal to 1%.

In one aspect, the pharmaceutical composition consists of glucose, sodium bicarbonate, and water, where pH is from 6.7 to 7.7 and where pH is adjusted with a pH adjusting agent such as carbon dioxide, where the composition is stable after storage for at least 3 months at room temperature, as demonstrated by determining by HPLC analysis the amount of fructose present in the pharmaceutical composition at 3 months, and wherein the amount of the fructose present after 3 months is less than or equal to 3%.

In one aspect, the pharmaceutical composition consists of glucose and sodium bicarbonate, where pH is from 6.7 to 8.5 and where pH is optionally adjusted with a pH adjusting agent such as carbon dioxide, and where pH changes by less than 0.3 pH units after storage for at least 3 months at room temperature, is stable after storage for at least 3 months at room temperature, as demonstrated by determining the amount of fructose present in the pharmaceutical composition at 3 months, and wherein the amount of the fructose present after 3 months is less than or equal to 1%.

Typically, ready to use pharmaceutical compositions have osmolality from 250 to 350 mOsm/kg.

In some aspects, the ready to use pharmaceutical compositions further comprise one or more osmolality agents. Exemplary osmolality agents for use in ready to use pharmaceutical compositions include, but are not limited to, anhydrous or hydrous forms of sodium chloride, sucrose, xylitol, glycerol, sorbitol, mannitol, potassium chloride, calcium chloride, and magnesium chloride.

In some aspects, the formulation comprises amino acids. In one aspect, the amino acid comprises arginine, tryptophan, glycine, phenylalanine, tyrosine, proline, taurine, lysine, histidine, glutamine, serine, methionine, alanine, aspartic acid, glutamic acid and pharmaceutically acceptable salts thereof.

In an aspect, amino acids may be histidine, glycine, or a combination thereof.

In one aspect, the formulation may comprise amino acids which do not have side chains.

In one aspect, the formulation may comprise N-acetyl-D-Alanine.

In some aspects, the amino acids may be in an L configuration, while in some other aspects the amino acids may be in a D configuration.

In one aspect, glucose and at least one amino acid are in molar ratio of 1:0.5, 1:1, 1:1, 1:3, 1:4, 1:5, 1:6, 1:7, 1:8, 1:9, 1:10, 1:11, 1:12, 1:13, 1:14 or 1:15.

In one aspect, the composition is an isosmotic composition. It is to be understood that the term "isosmotic" in accordance with the present disclosure is meant having similar osmolality to the physiologic osmolality of blood.

In one aspect, the volume of the composition may be from 10 ml to 1000 ml or even 2000 ml. In one aspect, the volume of the composition is 500 ml to 1000 ml.

In one aspect, the volume of the composition is 500 ml.

In one aspect, the volume of the composition is 1000 ml.

This disclosure also provides a method for stabilizing glucose in a pharmaceutical composition by mixing glucose with a solution having a pH in the range of 6.7 to 8.5 and storing said composition in a single unit container.

This disclosure also provides process for manufacturing pharmaceutical formulations disclosed herein. In various embodiments, the process may comprise the steps of mixing glucose with a solution having pH in the range of 6.7 to 8.5 and optionally other pharmaceutical ingredients.

In another aspect, the pharmaceutical formulation may be manufactured by any process known to the person skilled in the art.

The disclosure also relates to the packaging of any of the above pharmaceutical formulations. In one aspect, the packaging may comprise a primary packaging in which the composition is stored. The terms "container" and "primary packaging" are used herein interchangeably. In an aspect, the liquid pharmaceutical formulation may be packaged in a single unit bag which is ready to be administered to a patient.

In an aspect, the formulation is stored in a container, e.g., a single use container, such as intravenous bags and syringes, which are preferably polymer-based. In an aspect, the formulation is packaged in a flexible plastic bag. In one aspect, the material of the bag is PVC-free. In one aspect, the formulation is not in contact with a PVC material of the bag. In one aspect, the container is an intravenous bag that does not have any PVC containing components in contact with the pharmaceutical composition. In one aspect, the primary packaging is made of polypropylene, polyethylene, polystyrene, a polyolefin material, or a combination thereof. In one aspect, the inner layer of the primary packaging is made of polypropylene, polyethylene, polystyrene, a polyolefin material, or a combination thereof.

In one aspect, the headspace of the primary packaging is filled with atmosphere, carbon dioxide ($CO_2$), nitrogen ($N_2$), argon, or any combination thereof.

In one aspect, the headspace of the primary packaging is filled with $CO_2$.

In one aspect, the closure of the primary packaging is made of rubber.

In one aspect, the closure of the primary packaging is made of synthetic rubber.

In one aspect, the packaging may additionally comprise a secondary packaging. The term "secondary packaging" and "overwrap" are used interchangeably. In an aspect, the secondary packaging substantially surrounds the primary container housing the composition of the disclosure.

In one aspect, the primary packaging may, optionally, further comprise a light barrier. In one aspect, the secondary packaging may, optionally, further comprise a light barrier. A preferred light barrier is an aluminum secondary packaging.

In one aspect, the secondary packaging comprises a gas barrier material.

In one aspect, the space between primary and secondary packaging is filled with atmosphere, $CO_2$, $N_2$, argon, or any combination thereof.

In one aspect, the space between primary and secondary packaging is under vacuum.

In one aspect, the primary packaging, secondary packaging or a combination thereof has a water vapor transmission rate (WVTR) 3.0 $g/m^2 \times day$, in particular <3.0 $g/m^2 \times day$. In one aspect, the primary packaging, secondary packaging or combination thereof has a WVTR from 3 $g/m^2 \times day$ to 0 $g/m^2 \times day$, from 2 $g/m^2 \times day$ to 0 $g/m^2 \times day$, from 1 $g/m^2 \times day$ to 0 $g/m^2 \times day$. In one aspect, he primary packaging, secondary packaging or combination thereof has a water vapor transmission rate less than 1 $g/m^2 \times day$.

The "water vapor transmission rate", also abbreviated as "WVTR", as used herein may be determined by ASTM F1249 or ISO 15106.

In one aspect, the primary packaging, secondary packaging or a combination thereof has an oxygen transmission rate (OTR) 3 $cm^3/(m^2 \times d \times bar)$. In one aspect, the primary packaging, secondary packaging, or a combination thereof has an OTR from 3 $cm^3/(m^2 \times d \times bar)$ to 0 $cm^3/(m^2 \times d \times bar)$, from 2 $cm^3/(m^2 \times d \times bar)$ to 0 $cm^3/(m^2 \times d \times bar)$, from 1 $cm^3/(m^2 \times d \times bar)$ to 0 $cm^3/(m^2 \times d \times bar)$. In one aspect, the primary packaging, secondary packaging, or a combination thereof has an OTR rate less than 1 $cm^3/(m^2 \times d \times bar)$. The "oxygen transmission rate", also abbreviated as "OTR", as used according to the present invention may be determined by ASTM F1927 or ISO 15105.

In particular, the primary packaging, secondary packaging, or a combination thereof may be completely impermeable for carbon dioxide.

Parenteral products generally need to be sterile since the products are injected or infused into patients. There are several ways such products can be sterilized; the most common ways are either by terminal sterilization, or by aseptic filling of the container, e.g., a flexible plastic container.

In one aspect, formulations according to the disclosure are aseptically filled into sterilized containers. Aseptic manufacture of the sterile product means that the packaging material is sterilized and then a sterile product is filled into the packaging material under aseptic conditions. Sterilization of flexible plastic containers can be done by different irradiation techniques for example electron beam (beta irradiation), gamma-ray, and X-ray irradiation.

In one aspect, liquid composition may be sterilized by filtration through a 0.2 µm filter followed by aseptic filling of the liquid formulation into sterilized flexible plastic containers.

In terminal sterilization, autoclaving is normally used. In an aspect, autoclaving is a technique where the product is placed under pressurized saturated steam at 121 degrees Celsius for a period of time that can vary but would normally be up to 15 minutes, or more.

In one aspect, the liquid formulation of glucose is packaged into a container. In one aspect, the container is single unit dose container. In one aspect, the container is single unit dosage container for parenteral administration.

In one aspect, the present disclosure provides a method of treating humans by administering an effective dose of the glucose formulation by a parenteral route of administration.

In one aspect, the present disclosure provides a method of treating humans by administering a ready-to-administer, effective dose of a glucose formulation as described herein by IV injection.

In one aspect, present disclosure provides a method for administering a liquid composition comprising glucose to a subject, the method comprising drawing a composition as described herein from a ready-to-administer single unit container and administering the composition into the subject using an IV infusion.

In one aspect, a liquid composition comprises a compound with antiacidotic action may be used for the treatment of metabolic acidosis. In one aspect, said compound may be selected from bicarbonate salts and mixture thereof.

Metabolic acidosis is a serious electrolyte disorder characterized by an imbalance in the body's acid-base balance. Metabolic acidosis has three main root causes: increased acid production or ingestion, loss of bicarbonate, and a reduced ability of the kidneys to excrete excess acids. Metabolic acidosis can lead to acidemia, which is defined as an arterial blood pH that is lower than 7.35.

Treatment of metabolic acidosis depends on the underlying cause and should target reversing the main process.

In one aspect, the compound with antiacidotic action may be sodium bicarbonate, sodium acetate, or tromethamine.

Described herein is a parenterally administrable solution suitable for use in the treatment of mammalian acidosis, which solution comprises glucose and sodium bicarbonate in a molar ratio of glucose to sodium bicarbonate of approximately 1:0.2 to 1:0.8 dissolved in a pharmaceutically acceptable diluent.

In one aspect, the compositions described herein can be used to treat metabolic acidosis. In an aspect, the composition for treatment of metabolic acidosis comprises glucose, sodium bicarbonate and not more than 1% of fructose after storing the composition for 3 months at room temperature. In one aspect, the composition for treatment of metabolic acidosis comprises glucose, sodium bicarbonate, and less than or equal to 1% of fructose after storing the composition for 3 months at room temperature. In one aspect, the composition for treatment of metabolic acidosis comprises glucose, sodium bicarbonate, and less than or equal to 1% of fructose after storing the composition for 3 months at room temperature and has a pH from 6.7 to 8.5. Fructose can potentially worsen initial state of acidosis and therefore impact the efficacy of the drug (treatment). Impact depends on the amount and rate of infusion of fructose and clinical condition of the patient.

In one aspect, the present disclosure provides a method of treating a population of humans having metabolic acidosis by administering an effective dose of the liquid composition comprising glucose and sodium bicarbonate in accordance with this disclosure by a parenteral route of administration.

In one aspect, the present disclosure provides a method of treating a population of humans having drug intoxication by administering an effective dose of the liquid composition comprising glucose and sodium bicarbonate in accordance with this disclosure by a parenteral route of administration.

In one aspect, the present disclosure provides a method of treating a population of humans having severe diarrhea by administering an effective dose of the liquid composition comprising glucose and sodium bicarbonate in accordance with this disclosure by a parenteral route of administration.

In one aspect, the present disclosure provides a method of treating a human having metabolic acidosis by administering the aqueous composition comprising glucose, sodium bicarbonate and water, wherein the pH of the composition is from 6.7 to 8.5, and the pH of the composition changes by less than or equal to 0.3 unit after storing the composition for 3 months at room temperature.

In one aspect, the present disclosure provides a method of treating a human having metabolic acidosis, wherein the method comprises: (i) providing the aqueous composition comprising glucose, sodium bicarbonate and water in a single unit dosage form, wherein the pH of the composition is from 6.7 to 8.5, and where the composition contains less than or equal to 1% of fructose analyzed by the HPLC after storing the composition for 3 months at room temperature.

In one aspect, the present disclosure provides a method of treating a human having metabolic acidosis, wherein the method comprises: (i) providing the aqueous composition comprising glucose, sodium bicarbonate in concentration from 4 mg/ml to 15 mg/ml and water in a single unit dosage form, wherein the pH of the composition is from 6.7 to 8.1, and the composition contains less than or equal to 1% of fructose after storing the composition for 3 months at room temperature; (ii) administering portion of the composition to a human.

In one aspect, the present disclosure provides a method of treating a human having metabolic acidosis, wherein the method comprises: (i) providing the aqueous composition comprising glucose, sodium bicarbonate in concentration from 4 mg/ml to 15 mg/ml and water in a single unit dosage form, wherein the pH of the composition is from 6.7 to 8.1; (ii) storing the composition for 3 months at room temperature; and the composition contains less than or equal to 0.3% of fructose after storing the composition for 3 months at room temperature; (ii) administering portion of the composition to a human.

Also within the scope of the disclosure is use of pharmaceutical formulations of glucose, as disclosed herein, where such use comprises administering to the patient a therapeutically effective amount of formulations according to this invention or administering to the patient a therapeutically effective amount of preparation prepared from a pharmaceutical composition of the present invention.

In an aspect, a liquid formulation comprising glucose may be used as a nutritional solution, a solution for peritoneal dialysis, a renal replacement therapy solution such as for hemofiltration and hemodiafiltration, a solution for treatment of metabolic acidosis, and the like.

In an aspect, formulations described herein are intended to be administered parenterally. In an aspect, formulations described herein are intended to be administered via injection or infusion, for example intravenously.

All of the numbers used herein are modified by the term "about." This means that each number includes minor variations as defined ±10% of the numerical value or range in question.

Other objects, features and advantages will become apparent from the following detailed description and examples. It should be understood, however, that the detailed description and the examples, while indicating specific embodiments, are given by way of illustration only, and are not intended to limit the breadth or scope of the concepts in any manner.

Examples

Experimental Methods

Preparation of compositions comprising glucose: All formulations presented in the examples below were prepared by providing a liquid solution of glucose and optionally at least one pharmaceutical ingredient, all in targeted concentrations. If necessary, pH was adjusted to achieve the desired pH range.

The prepared compositions were transferred into containers, such as vials, or bags to achieve a desired amount of active component per container.

Analytical Methods

After preparation, an initial time point level of glucose, its impurities and/or other pharmaceutical ingredients was determined by appropriate analytical techniques, and afterwards the containers were loaded to stability chambers at different storage conditions: 60° C., 40° C., 30° C., and 25° C.

In order to determine the stability of the pharmaceutical ingredient in the formulations according to the present disclosure, containers were taken from the stability chambers at various time points, such as 1 day, 1 month, 2 months, 3 months, 4 months, 6 months, etc., and analyzed by appropriate analytical techniques.

Chromatographic purity of glucose was determined by HPLC using Refractive Index Detector (RID).

The conditions for the method are listed below.
Chromatographic Purity of Glucose
  Chromatographic system:
    Column: Waters, Acquity® BEH Amide, 130 Å, 1.7 μm, 3 mm×150 mm
    Mobile phase: Acetonitrile: Water, 80:20, plus 0.2% Ammonium hydroxide
    Flow rate: 0.150 mL/min
    Run time: 60 min Detection: RID
Column Temperature: 45° C.
Detector temperature: 45° C.
Calculation of Purity Drop of the Main Peak Area % of glucose and substances structurally similar to glucose as determined using refractive index detection.

Area percent of glucose and individual substances structurally similar to glucose is calculated using the following equation:

$$\% \text{ area} = (A_i/A_{tot})100\%$$

where;
% area=Area % of an individual peak;
$A_i$=Peak area of an individual peak; and
$A_{tot}$=total sample peak area of glucose and all substances structurally similar to glucose Calculate the percent purity of glucose in Area percent using the following equation:

$$\% \text{ glucose} = 100\% - \% \text{ total substances structurally similar to glucose.}$$

Analytical Procedure for 5-HMF

Analytical method for 5-HMF is in accordance with USP monograph for dextrose injection as official from Jan. 1, 2022.

Analytical Procedure for Sodium Bicarbonate

An accurately measured volume of test sample is titrated with 1M hydrochloric acid. The endpoint is determined potentiometrically. Each ml of 1M hydrochloric acid is equivalent to 84.01 of sodium bicarbonate. The content of sodium bicarbonate is expressed as % target concentration.

% target concentration was calculated as follows:

$$\% \text{ target concentration} = (\text{Determined concentration of sodium bicarbonate at predetermined time point})/(\text{Target concentration of Sodium bicarbonate}) \times 100\%$$

LIST OF ABBREVIATIONS IN TABLES

M—Month
% TC—target concentration (of sodium bicarbonate)
ND—not detected
N/A—not analyzed
Abs—Absorbance

EXAMPLES

In below Examples, glucose is added in a form glucose monohydrate or glucose anhydrous.

Example 1

Ready-to-administer formulations of glucose were prepared by dissolving glucose in water for injection under predefined conditions. The contents were stirred using a magnetic stirrer. If necessary, the pH was adjusted to a predefined pH. The solution was mixed to ensure homogeneity, water for injection (WFI) was added to make up the predefined volume, and the solution was filtered through a 0.2 μm filter and transferred to a container.

Formulations were then stored at a predetermined temperature and stability was determined at time points such as 1 month, 2 months, 3 months and further.

Example 2

Formulations comprising glucose were prepared by dissolving glucose and predetermined other ingredients in WFI under predefined conditions. The contents were stirred using a magnetic stirrer. If necessary, the pH was adjusted with carbon dioxide to provide the predefined pH. The solution was mixed to ensure homogeneity, WFI was added to make up the predefined volume, and the solution was filtered through a 0.2 μm filter and transferred to a container. Some formulations stored of plastic containers were overwrapped and in some cases the space between the overwrap and the plastic container is vacuumed. Formulations were then stored at a predetermined temperature and stability was determined at time points such as 24 hours, 1 month, 2 months, 3 months and further.

TABLE 1

STABILITY DATA OF FORMULATIONS COMPRISING GLUCOSE AND SODIUM BICARBONATE AT TARGETED CONCENTRATIONS AND PH. ALL FORMULATIONS WERE CONTAINED IN 10 ML GLASS VIALS

| Formulation | Condition | Time point | pH (7.0-8.5) | ΔpH | Glucose Area % | Fructose Area % |
|---|---|---|---|---|---|---|
| NaHCO₃ | START | START | 7.01 | | N/A | N/A |
| 12.6 mg/ml | 60° C. | 24 h | 7.06 | 0.05 | 99.5 | 0.53 |
| D-glucose | 40° C. | 1M | 7.17 | 0.17 | 99.1 | 0.83 |
| monohydr. | 25° C. | 3M | 7.14 | 0.14 | 99.8 | 0.16 |
| 36.6 mg/ml | 30° C. | 3M | 7.17 | 0.17 | 99.5 | 0.35 |
| NaHCO₃ | START | START | 7.02 | | N/A | N/A |
| 12.6 mg/ml | 60° C. | 24 h | 7.06 | 0.04 | 99.5 | 0.53 |
| D-glucose | 40° C. | 1M | 7.20 | 0.18 | 98.4 | 0.88 |
| monohydr. | 25° C. | 3M | 7.14 | 0.12 | 99.9 | 0.13 |
| 24.0 mg/ml | 30° C. | 3M | 7.17 | 0.15 | 99.6 | 0.32 |
| NaHCO₃ | START | START | 7.85 | | N/A | N/A |
| 4.2 mg/ml | 60° C. | 24 h | 7.72 | −0.13 | 97.8 | 2.18 |
| D-glucose | 40° C. | 1M | 7.94 | 0.09 | 96.2 | 3.8 |
| monohydr. | 25° C. | 3M | 7.99 | 0.14 | 99.2 | 0.78 |
| 36.6 mg/ml | 30° C. | 3M | 8.01 | 0.16 | 98.2 | 1.76 |
| NaHCO₃ | START | START | 7.55 | | N/A | N/A |
| 4.2 mg/ml | 60° C. | 24 h | 7.55 | 0.00 | 97.7 | 1.4 |
| D-glucose | 40° C. | 1M | 7.69 | 0.14 | 97.8 | 2.2 |
| monohydr. | 25° C. | 3M | 7.72 | 0.17 | 99.6 | 0.40 |
| 36.6 mg/ml | 30° C. | 3M | 7.79 | 0.24 | 98.9 | 1.13 |
| NaHCO₃ | START | START | 7.34 | | N/A | N/A |
| 4.2 mg/ml | 60° C. | 24 h | 7.38 | 0.04 | 99.0 | 1.0 |
| D-glucose | 40° C. | 1M | 7.48 | 0.13 | 98.7 | 1.3 |
| monohydr. | 25° C. | 3M | 7.52 | 0.18 | 99.8 | 0.22 |
| 36.6 mg/ml | 30° C. | 3M | 7.53 | 0.18 | 99.4 | 0.59 |
| NaHCO₃ | START | START | 7.05 | | N/A | N/A |
| 4.2 mg/ml | 60° C. | 24 h | 7.11 | 0.06 | 99.5 | 0.50 |
| D-glucose | 40° C. | 1M | 7.15 | 0.11 | 99.2 | 0.80 |
| monohydr. | 25° C. | 3M | 7.23 | 0.18 | 99.9 | 0.12 |
| 36.6 mg/ml | 30° C. | 3M | 7.21 | 0.17 | 99.8 | 0.25 |

TABLE 2

STABILITY DATA OF FORMULATIONS COMPRISING GLUCOSE AND SODIUM BICARBONATE AT TARGETED CONCENTRATIONS AND PH. ALL FORMULATIONS WERE FILLED IN 50 ML FLEXIBLE PLASTIC BAGS. AFTER FILLING THE FORMULATIONS IN BAGS, BAGS WERE OVERWRAPPED AND THE SPACE BETWEEN THE BAG AND THE OVERWRAP HAS BEEN PLACED UNDER VACUUM.

| Formulation | Condition | Time point | pH | ΔpH | % TC | Glucose area % | Fructose area % | 5-HMF abs at 284 nm |
|---|---|---|---|---|---|---|---|---|
| NaHCO₃ | 25° C. | START | 6.95 | | 99.7% | N/A | N/A | N/A |
| 4.2 mg/ml | | 3M | 7.05 | 0.1 | 98.4% | 100.0% | ND | 0.01 |
| D-glucose | | 4M | 7.06 | 0.11 | 97.3% | 99.9% | 0.10 | 0.00 |
| monohydr. | | 5M | 6.98 | 0.03 | 99.2% | 99.8% | 0.21 | 0.00 |
| 36.6 mg/ml | | 6M | 7.01 | 0.06 | 98.7% | 99.8% | 0.25 | 0.01 |
| | 40° C. | 3M | 7.00 | 0.05 | 96.8% | 99.1% | 0.95 | 0.01 |
| | | 4M | 7.05 | 0.10 | 96.6% | 98.1% | 1.92 | 0.02 |
| | | 5M | 6.96 | 0.01 | 97.5% | 97.4% | 2.56 | 0.04 |
| | | 6M | 6.99 | 0.04 | 97.9% | 96.9% | 3.13 | 0.07 |
| NaHCO₃ | 25° C. | START | 6.93 | | 99% | N/A | N/A | N/A |
| 8.4 mg/ml | | 3M | 7.07 | 0.14 | 100% | 100.0% | ND | 0.00 |
| D-glucose | | 4M | 7.08 | 0.15 | 98% | 100.0% | ND | 0.00 |
| monohydr. | | 5M | 7.07 | 0.14 | 100% | 99.8% | 0.16 | 0.00 |
| 24.0 mg/ml | | 6M | 7.10 | 0.17 | 101% | 99.8% | 0.21 | 0.01 |
| | 40° C. | 3M | 7.04 | 0.11 | 98.8% | 98.0% | 1.96 | 0.02 |
| | | 4M | 7.08 | 0.15 | 95.6% | 97.4% | 2.63 | 0.02 |
| | | 5M | 7.02 | 0.09 | 98.5% | 96.5% | 3.47 | 0.02 |
| | | 6M | 7.07 | 0.14 | 100.4% | 95.9% | 4.06 | 0.05 |
| NaHCO₃ | 25° C. | START | 7.07 | | 99.4% | 100.0% | ND | N/A |
| 4.2 mg/ml | | 3M | 7.15 | 0.08 | 100.0% | 100.0% | ND | N/A |
| D-glucose | | 6M | 7.14 | 0.07 | 99.9% | 99.7% | 0.32 | N/A |
| anhydr. | 40° C. | 3M | 7.08 | 0.01 | 98.5% | 98.0% | 2.0 | N/A |
| 33.3 mg/ml | | 6M | 7.08 | 0.01 | 98.1% | 95.4% | 4.6 | 0.04 |
| NaHCO₃ | 25° C. | START | 6.98 | | 99.6% | 100.0% | ND | N/A |
| 8.4 mg/ml | | 3M | 7.09 | 0.10 | 99.7% | 100.0% | ND | N/A |
| D-glucose | | 6M | 7.09 | 0.11 | 99.7% | 99.8% | ND | N/A |
| anhydr. | 40° C. | 3M | 7.07 | 0.09 | 99.5% | 97.7% | 2.3 | N/A |
| 21.8 mg/ml | | 6M | 7.12 | 0.13 | 99.1% | 94.9% | 5.1 | 0.04 |

The invention claimed is:

1. An aqueous composition stored in a single unit dosage container, where the aqueous composition consists of glucose in a concentration from 1 mg/ml to 50 mg/ml, sodium bicarbonate in concentration from 4 mg/ml to 15 mg/ml, water, and a pH adjusting agent to adjust the pH, wherein the pH of the composition is from 6.7 to 8.1,
wherein, after storing the composition for 3 months at room temperature, the composition contains less than or equal to 1% of fructose as determined by high pressure liquid chromatography (HPLC).

2. The aqueous composition according to claim 1, wherein, after storing the composition for 3 months at room temperature, the composition comprises less than or equal to 0.5% of fructose as determined by HPLC.

3. The aqueous composition according to claim 1, wherein the glucose is selected from anhydrous glucose and glucose monohydrate.

4. The aqueous composition according to claim 1, wherein the concentration of glucose is from 5 mg/ml to 50 mg/ml.

5. The aqueous composition according to claim 1, wherein the concentration of glucose is from 15 mg/ml to 40 mg/ml.

6. The aqueous composition according to claim 1, wherein the concentration of sodium bicarbonate is from 4.2 mg/ml to 12.6 mg/ml.

7. The aqueous composition according to claim 1, wherein the pH is from 6.7 to 7.7.

8. The aqueous composition according to claim 1, wherein, after storage for 3 months at room temperature, a sample solution from the composition has an absorbance of less than or equal to 0.25 at 284 nm of 5-hydroxymethyl-furfural.

9. The aqueous composition according to claim 1, wherein the pH adjusting agent is $CO_2$.

10. The aqueous composition according to claim 1, wherein the single unit dosage container is a flexible plastic container.

11. The aqueous composition according to claim 10, wherein the flexible plastic container is overwrapped with an overwrap.

12. The aqueous composition according to claim 11, wherein the space between the flexible plastic container and the overwrap is vacuumed.

13. The aqueous composition according to claim 1, wherein the composition has been aseptically filled into the single unit dosage container.

14. A method of treating a human having metabolic acidosis, the method consisting essentially of:
(i) providing the aqueous composition of claim 1; and
(ii) administering the composition to the human from the single unit dosage container.

15. A method of treating a human having metabolic acidosis, wherein the method consists essentially of: (i) preparing the aqueous composition in a unit dosage form, the composition consisting of glucose in a concentration from 1 mg/ml to 50 mg/ml, sodium bicarbonate in concentration from 4 mg/ml to 15 mg/ml, a pH adjusting agent, water, and a pH control agent to adjust the pH, wherein the pH of the composition is from 6.7 to 8.1; (ii) storing the unit dosage form for at last 3 months at room temperature after the preparation; and (iii) after storing, administering the unit dosage form to the human; wherein the unit dosage form that is administered to the human contains less than or equal to 1% of fructose as determined by HPLC.

* * * * *